United States Patent [19]

Schmid

[11] Patent Number: 5,279,721
[45] Date of Patent: Jan. 18, 1994

[54] APPARATUS AND METHOD FOR AN AUTOMATED ELECTROPHORESIS SYSTEM

[76] Inventor: Peter Schmid, 10431 Regent St., Los Angeles, Calif. 90034

[21] Appl. No.: 52,079

[22] Filed: Apr. 22, 1993

[51] Int. Cl.$^5$ .............. G01N 27/26; G01N 27/447
[52] U.S. Cl. .............. 204/182.8; 204/299 R; 435/6; 435/287; 436/43; 935/77
[58] Field of Search ............ 204/299 R, 182.8; 435/6, 287; 436/43; 935/77

[56] References Cited

U.S. PATENT DOCUMENTS

| | | | |
|---|---|---|---|
| 4,726,889 | 2/1988 | Love et al. | 204/182.8 |
| 4,911,816 | 3/1990 | Love et al. | 204/299 R |
| 5,188,963 | 2/1993 | Stapleton | 204/299 R |

FOREIGN PATENT DOCUMENTS

| | | | |
|---|---|---|---|
| 134622 | 3/1985 | European Pat. Off. | 204/299 R |
| 3805808 | 2/1988 | Fed. Rep. of Germany | 435/6 |

OTHER PUBLICATIONS

R. K. Wilson et al. "Automation of Dideoxynucleotide DNA Sequencing Reactions Using a Robotic Workstation." Biotechniques, vol. 6 No. 8 (1988) 776–785.

Primary Examiner—John Niebling
Assistant Examiner—John S. Starsiak, Jr.
Attorney, Agent, or Firm—Harold L. Jackson

[57] ABSTRACT

An automated electrophoresis and transfer apparatus for separating macromolecules in accordance with their molecular weight and transferring the same to a transfer membrane includes a housing having a perforated intermediate horizontal partition defining an upper reservoir and a lower chamber. A pair of spaced electrodes are provided for generating a horizontal electrical field. A pump is connected between a plurality of containers and the reservoir for sequentially pumping the chemical solutions within the container into the reservoir. A transfer membrane is positioned over the partition and an impermeable sheet is interposed between the membrane and the gel member and withdrawn prior to the transfer operation. A pump provides a small over pressure within the lower chamber which in cooperation with the impermeable sheet substantially prevents chemical solutions from penetrating the transfer membrane prior to the transfer operation. A vacuum pump provides a low pressure within the lower chamber and a pair of vertically spaced electrodes provides a vertical electrical field across the gel member and transfer membrane during the transfer operation.

27 Claims, 4 Drawing Sheets

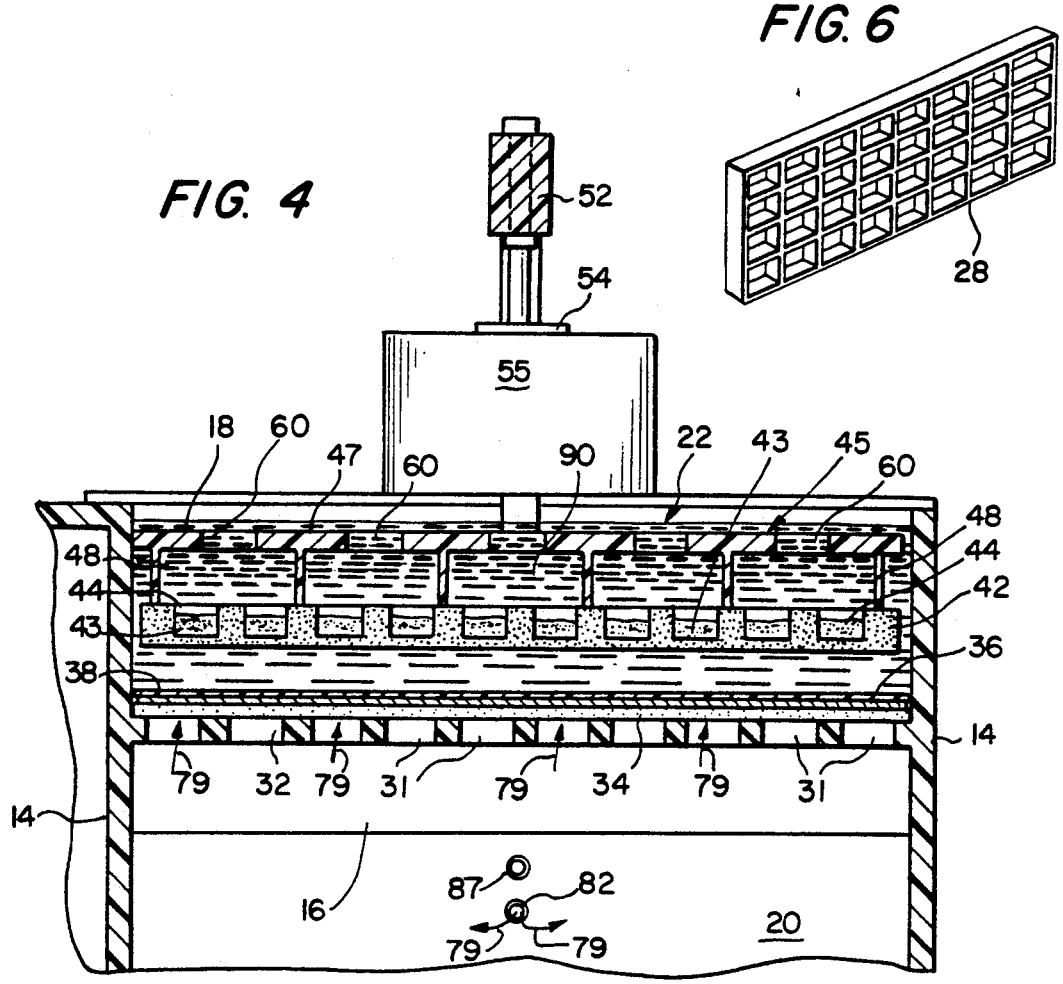
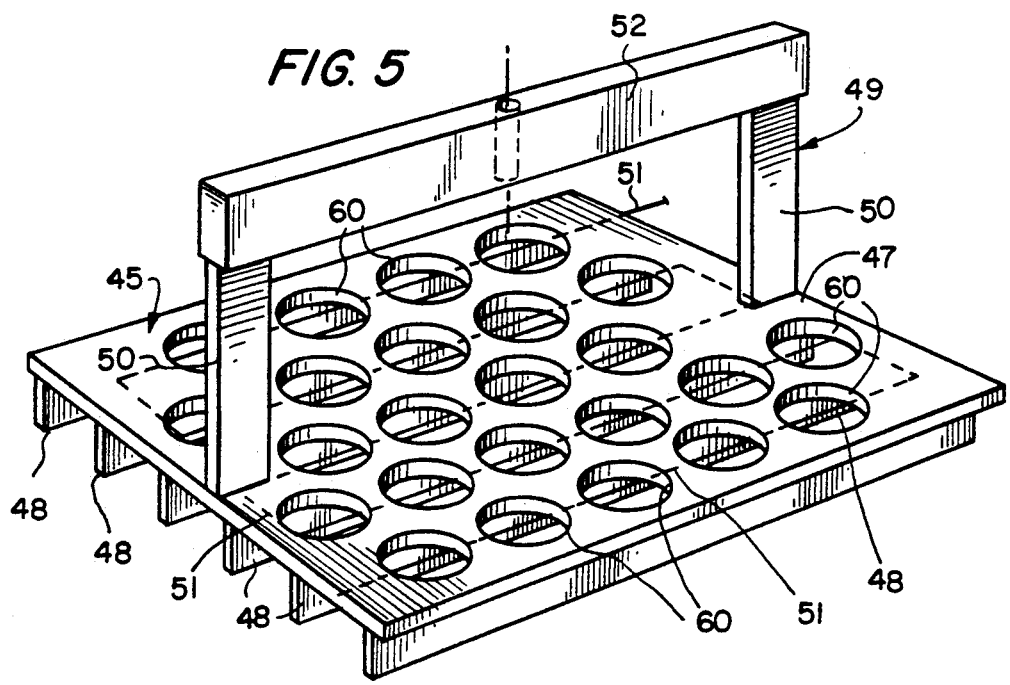

APPARATUS AND METHOD FOR AN AUTOMATED ELECTROPHORESIS SYSTEM

BACKGROUND OF THE INVENTION

1. Field of the Invention

The present invention relates generally to an apparatus and process for conducting electrophoresis and transfer and more particularly to an apparatus and process for automatically conducting electrophoresis and transfer whereby the handling of the gel is substantially reduced.

2. Description of the Prior Art

As is well known in the art, various problems and difficulties have been encountered in conducting electrophoresis and transfer of macromolecules such as nucleic acid DNA/RNA fragments. A popular electrophoresis and transfer procedure is commonly referred to as the Southern Blot Technique.

Basically, the electrophoresis procedure provides for the migration of charged macromolecules through a suitable retarding medium under the influence of a horizontal electro-transfer function (i.e., an electric field) During the horizontal transfer function, the macromolecules of high molecular weight migrate at a slower rate through the medium than do the macromolecules of lower molecular weight. The normal retarding medium comprises a conventional electrophoresis gel that is supported within a tray. Several wells are formed transversely across the gel, the wells being adapted to receive individual DNA, RNA or protein samples for processing. The samples are positioned so as to be subjected to the electrophoresis process, at which time the tray is at least partially filled with an electrolyte buffer. Electrodes are commonly positioned at each end of the gel tray. A sufficient voltage difference is applied to the electrodes to cause the macromolecules of the sample to migrate from the wells longitudinally along the gel, so that they are separated according to their molecular weight.

At this point, the gel is generally removed from its tray. Macromolecules such as DNA/RNA fragments are then generally depurinated i.e., broken into smaller fragments and subsequently denatured i.e., separated into single strands for subsequent transfer onto a suitable membrane.

There are many occasions in the steps of conventional electrophoresis, depuration, denaturation and transfer of the macromolecules to the membrane that cause difficulties which allow for errors as well as loss of considerable time and money. Various devices have been provided previously for carrying out electrophoresis such as can be found in U.S. Pat. No. 4,415,418.

In U.S. Pat. No. 4,726,889 to J.D. Love et al there is disclosed an apparatus for carrying out horizontal gel electrophoresis for separation and subsequent vacuum-assisted transportation of macromolecules to a support membrane to facilitate detection The entire procedure is conducted in one cartridge.

U.S. Pat. No. 4,911,816 also to J.D. Love et al discloses an apparatus to very similar to that of the above noted patent to J.D. Love et al. This application is a continuation of application Ser. No. 077,240, now abandoned, which is a continuation-in-part of U.S. Pat. No. 4,726,889 and U.S. Pat. No. 4,756,809.

The above referenced patents do not allow for a fully automatic procedure. To allow for a fully automatic electrophoresis operation having high-quality results, different and additional sophisticated features are necessary. In order to achieve a truly automatic apparatus for Southern blotting (an apparatus that will operate all by itself after loading the gel until the completion of the transfer) it is necessary to find ways to prevent any liquid from penetrating into the binding membrane under the gel and/or into the mechanical support platform that has to previous for liquid to allow suction blotting.

There are several independent reasons for this requirement:

1. During electrophoresis, the electrolyte buffer will completely or at least partially penetrate into the space under the gel. This is turn will cause deviations of the electric field lines that will follow the nonlinear boundaries of the lower liquid surface. As a result of this the macromolecule (e.g., DNA) bands of interest will at least partially exit the gel on its lower surface, thereby binding them in wrong places to any accessible membrane positioned under the gel. The result will often be a messy, unreliable image of the band patterns that are to be transferred later in the process.

Another problem is inhomogeneity of field strength due to said field distortions, leading to deviations and errors in migration distances.

In the actual operation of the apparatus disclosed in the J.D. Love et al patents there is no continuous automatic operation provided because the DNA binding membrane cannot be present during the electrophoresis and chemical treatments for the reasons discussed above. This membrane is manually positioned under the gel after all the chemical treatments of the gel are completed.

2. Another reason why the membrane needs to be separated from the gel is that, during the depurination and denaturation steps, strong chemicals would contact the membrane and alter its later binding performance in ill defined ways, if not completely destroying its binding characteristics.

Accordingly, after reviewing the following disclosure it will be readily understood that the present invention provides various unique operating structures and processing features which make it possible to construct a truly and fully automatic electrophoresis, chemical treatment and transfer apparatus as heretofore not found in the art.

OBJECTIVES OF THE INVENTION

An important objective of the present invention to provide a single apparatus wherein electrophoresis, depurination, denaturation and transfer to a membrane are performed completely under a continuous automatic step-by-step procedure, and wherein the time cycle is significantly reduced when compared to other known processes of this character.

Another object of the present invention is to provide an apparatus of this character that eliminates the difficulties generally found in association with prior art methods and apparatuses, more particularly with respect to the handling of the gel and further steps of the process.

Still another object of the invention is to provide a single automatically operated electrophoresis and transfer apparatus that includes the use of a chemically inert separation sheet that is adapted to be automatically removed by means of a pulling device before the suction transfer is initiated.

A further object of the invention is to provide the mechanical features of a moveable separation sheet combined with an ambient-overpressure system so that liquid in the upper reservoir is not lost or allowed to permeate downwardly into an air chamber located below the reservoir.

It is still a further object of the present invention to provide an electrophoresis apparatus of this character that includes a dampening device which is defined by a finely regulated overpressure system having an air pump arranged to communicate with the lower chamber and wherein air is continually released from an inverted hydrostatic regulator "generating a very constant and precisely regulated pressures". This dampening is necessary to remove ripples and rapid fluctuations originating in the overpressure generating pump, for which the hydrostatic pressure regulating system would be to inert to react. The lower chamber further serves as a temporary reservoir for the necessary recycling of liquid during the transfer mode. That is, it is necessary to make the transfer liquid that passes through the gel into the lower chamber to be pumped back to the upper reservoir so as to continue the transfer cycle for as many hours as might be required to complete a transfer due to the wide variety of gel conditions.

A still further object of the present invention is to provide an apparatus of this character that includes the capacity to pour and allow the gel to set inside the electrophoresis chamber. This is important if very thin gels are to be used, as thin gels tend to break during the transfer from the gel caster to the electrophoresis chamber.

A still further object of the invention is to provide an apparatus in which the common limitations and difficulties in faithful and complete transfer of gel fragments are overcome through the combined use of the vertical forces of hydrodynamic and electrical field transfer both of these transfer methods alone have their specific limitations and combined not only allow the complete i.e., quantitative transfer that is necessary for quantitative studies of band intensities, but also extends the range of gels, from which such a transfer is possible to very high (up to 4%) agarose gel concentrations which are now in use to separate very small fragments of DNA/RNA with high resolution. This reduces the time necessary for the transfer and increase the sharpness of bands as they arrive on the recipient membrane, because lateral diffusion occurs during the transfer step.

Yet a further object of the present invention is to provide an apparatus of this character that includes a gel weight that properly positions the gel both during the electrophoresis and transfer steps, and further allows the gel to float in a solution so as to penetrate both the upper and lower sides of the gel during the chemical treatment cycles.

The present invention has a further feature wherein there is included an automatically positioning and removable gel weight. The gel weight is a substantially rectangular plastic structure having the approximate dimensions of the gel. The gel weight includes a plurality of longitudinal rib members located on the underside in thin lines parallel to the electrical field lines so as to contact or engage the gel and to allow evaporation of the electrophoresis buffer (for cooling purposes which is typically combined with a soft flow fan) during electrophoresis. This weight is automatically removed and/or positioned above the gel so that the gel can float as might be required during a particular cycle of the process, but yet be firmly repositioned at the times of electrophoresis and transfer.

SUMMARY OF THE INVENTION

In accordance with my invention an electrophoresis and transfer apparatus is arranged to provide a completely automatic system so that the gel is never required to be removed from the apparatus until the process is fully completed. Therefore, macromolecules such as nucleic acid fragments of DNA, RNA or protein samples may be prepared for subsequent hybridization using the process and apparatus of the invention as present herein whereby the fragments or proteins are finally attached to a membrane temporarily sealed off from and below a liquid reservoir. The reservoir is defined by a housing which is located above an air chamber, the reservoir being adapted to receive several processing solutions that are pumped into the reservoir sequentially by a control means. The reservoir is divided into three operating compartments which comprise a large compartment and two smaller outer compartments. One compartment receives the solutions as they are pumped from containers or bottles by way of conduits that deposit the solutions sequentially as required by the steps of the process. The solution travels through an enlarged central reservoir section or compartment defined by a pair of partitions having a multiplicity of passages or openings. The oppositely arranged smaller compartments are provided with a means to draw the solutions into a waste container as required during various steps of the process. This is all accomplished without the solution reaching the interior of the lower air chamber or wetting the membrane before the transfer.

The bottom wall of the reservoir central compartment is defined by the upper perforated wall of the air chamber through which a finely controlled air pressure is exerted. The air pressure is generated by an air pump which is automatically controlled to provide a regulated overpressure system. The reservoir section is adapted to receive a porous base support member supported on the upper perforated wall, whereby the over pressurized air is passed through the multiplicity of holes in the upper wall so as to aid in preventing the chemical solutions from passing through during the critical steps of the process. A transfer membrane is positioned over the base support member. This is the member that receives DNA and/or RNA fragments or proteins from the gel plate which is positioned over the transfer membrane. It is important to note that a suitable chemically inert separation sheet is removably positioned between the transfer membrane and the gel member. This separation sheet cooperates with the positive air pressure coming from the lower chamber to prevent any of the liquid chemical solutions in the central reservoir from penetrating into the transfer membrane. However, the inert separation sheet is adapted to be removed by means of a suitable pulling device before the vacuum transfer step of the process takes place.

The gel is normally floating in one of the selective solutions in the reservoir of the housing structure at the time the chemical treatment is being performed on the gel. An automatically positionable and removable gel weight having about the same rectangular dimensions of the gel is located above the gel member so as to engage the gel member when required during the process. The up and down movement of the gel weight is regulated by a suitable control device, whereby the gel weight is arranged to gently engage the gel member so as to guide it into engagement with the transfer membrane just as the separation sheet is removed.

In order to provide an accurate separation of the DNA fragments (or proteins etc.) according to molecular weight horizontally throughout the gel a pair of suitable electrodes are positioned in each end compartment of the reservoir. To aid in transferring the separated DNA fragments (or proteins etc.) to the transfer membrane, a vertical electro-transfer function is employed in cooperation with a vacuum-assist pump connected to the lower air chamber.

The characteristics and advantages of the invention are further sufficiently referred to in connection with the accompanying drawings, which represent one embodiment. After considering this example, skilled persons will understand that variations may be made without departing from the principles disclosed; and I contemplate the employment of any structures, arrangements or modes of operation that are properly within the scope of the appended claims.

BRIEF DESCRIPTION OF THE DRAWINGS

The features of the invention may best be understood by reference to the following description taken in conjunction with the accompanying drawings.

FIG. 4 is an enlarged cross-sectional view taken substantially along line 4—4 of FIG. 2;

FIG. 5 is a perspective view of the automatically operable gel weight frame structure; and FIG. 6 is a perspective view of one of the end wall members formed having a multiplicity of flow passages.

DESCRIPTION OF THE PREFERRED EMBODIMENT

Figure 1:
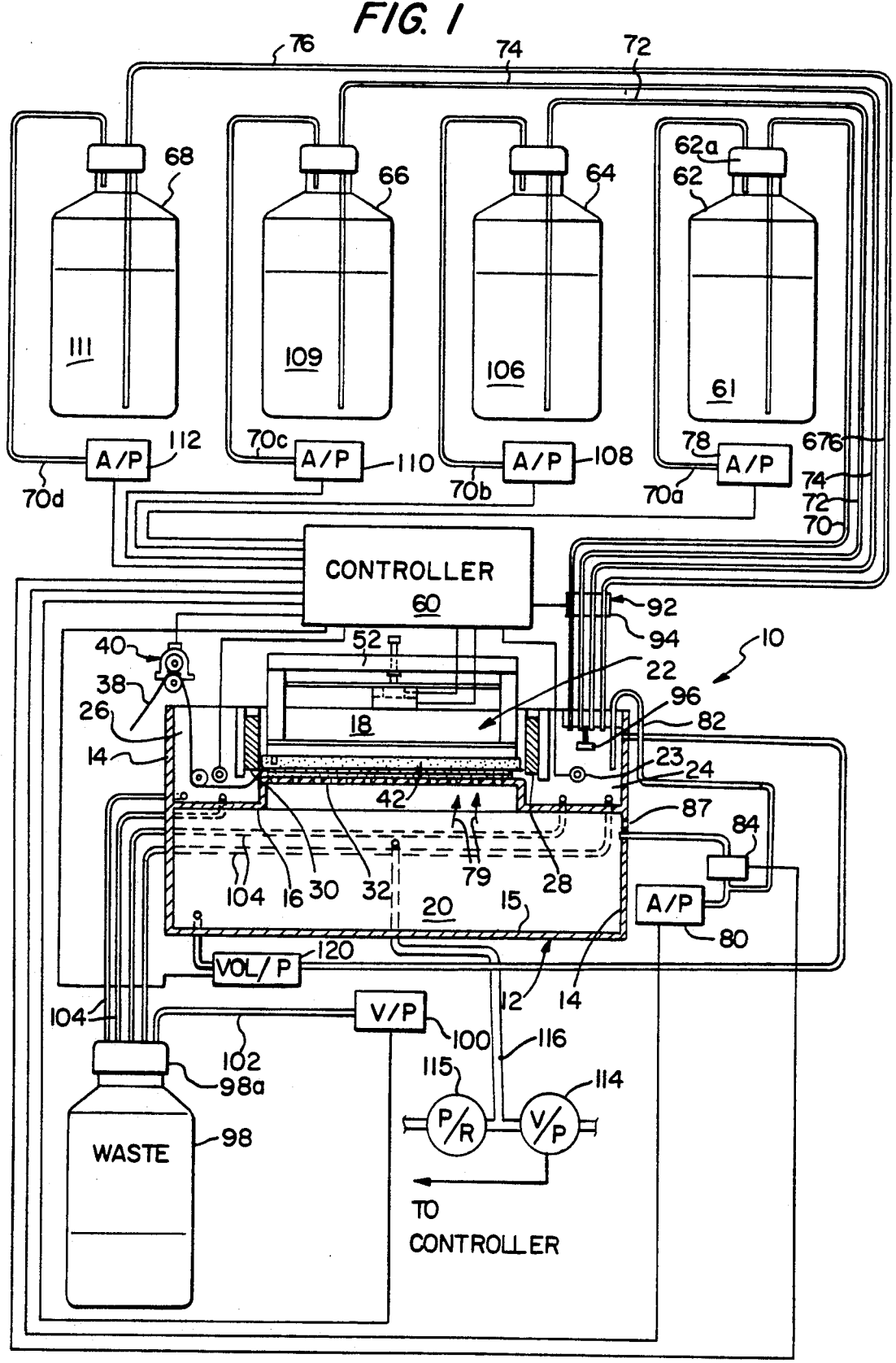
FIG. 1 is a schematic drawing of an apparatus in accordance with the invention particularly adapted for providing a continuous and automatic process for conducting electrophoresis and transfer of DNa fragments.
Figure 2:
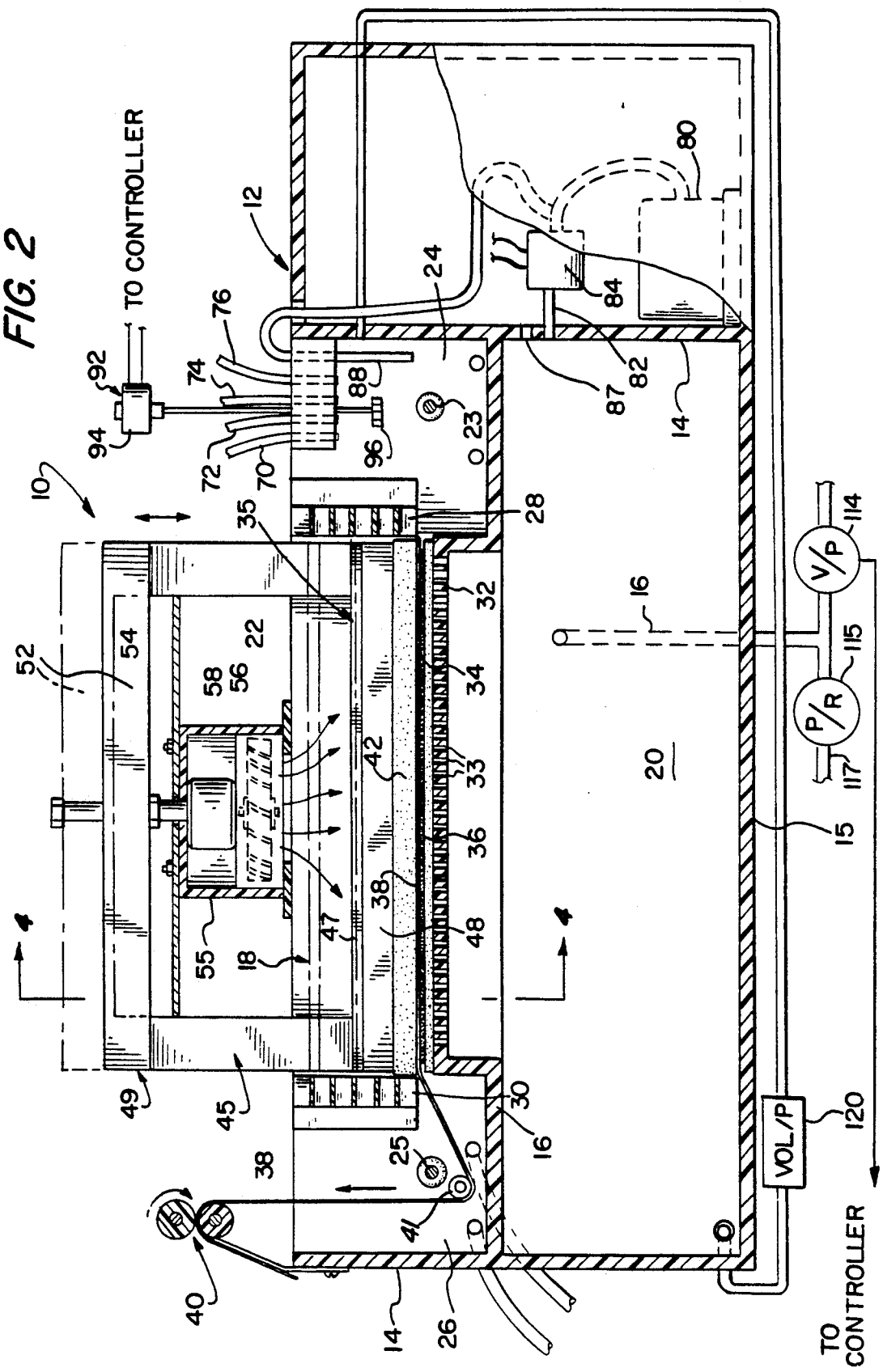
FIG. 2 is a enlarged cross-sectional view of the housing of the apparatus so as to illustrate the operative components therein.
Figure 3:
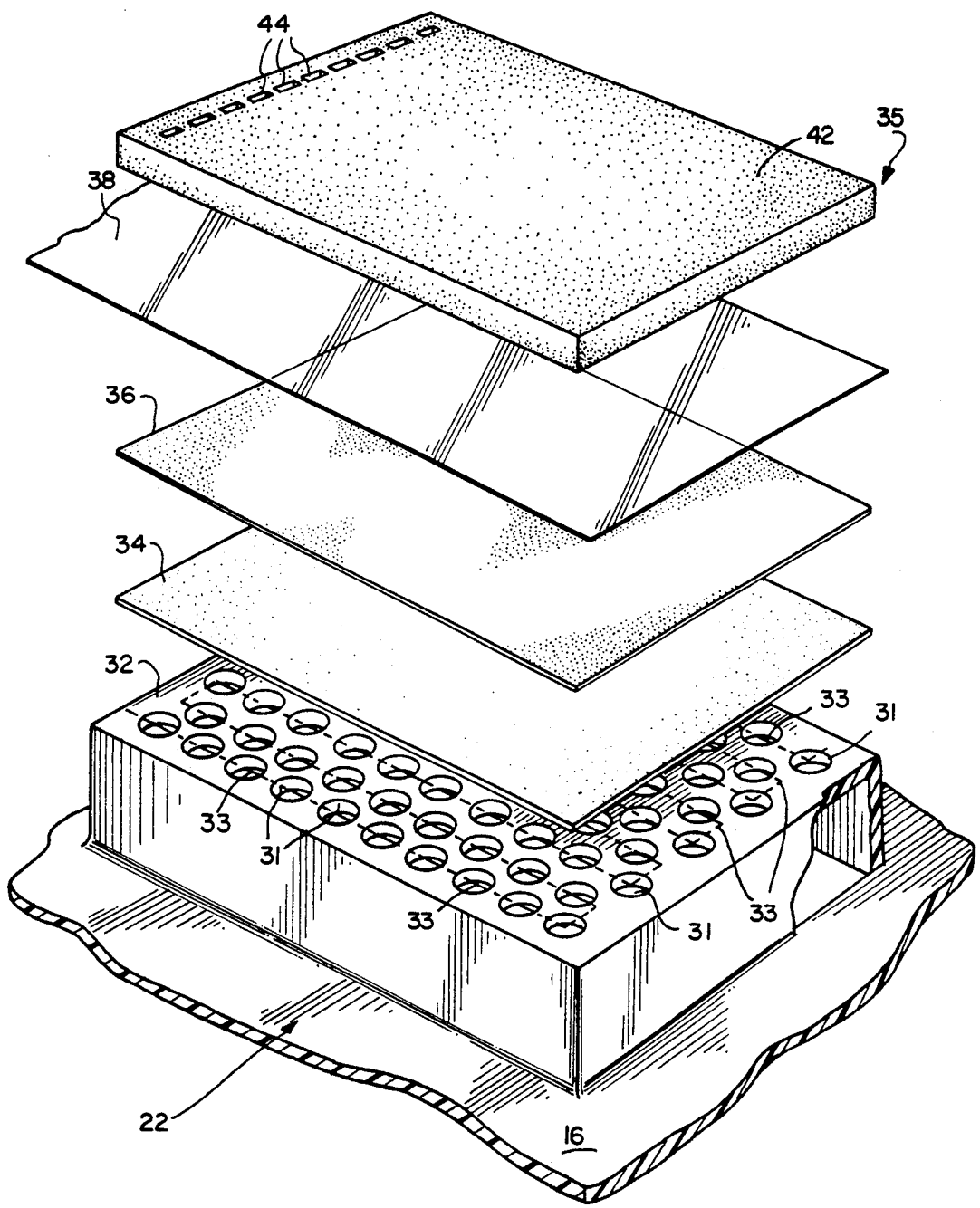
FIG. 3 is an exploded perspective view of the arrangement of the gel plate with respect to the removable separation sheet, the transfer membrane, the porous support base member and the upper perforated wall of the lower chamber of the housing.

Referring now to the drawings and more particularly to FIGS. 1, 2 and 3, there is shown the present invention which defines an apparatus 10 for automatically and sequentially conducting a horizontal electrophoresis for separation of macromolecules such as DNA fragment samples and the subsequent transfer of the DNA fragments or other macromolecules to a transfer membrane by means of a vertical-electrical field in combination with a vacuum-assist transfer means to facilitate the subsequent detection and identification of the macromolecules. One such automated detection system is described in my co-pending application Ser. No. 07/973,840 filed Nov. 9, 1992 for APPARATUS AND METHOD FOR ATTACHING A LABELED PROBE AND/OR ANTIBODY TO MACROMOLECULES.

Apparatus 10 comprises a housing 12 defined by a suitable arrangement of outer side wall members 14, bottom wall 15, and an intermediate wall or partition 16 which is substantially positioned horizontally within the side walls of housing 12 so as to define an upper reservoir 18 and a lower chamber 20. The upper reservoir 18 is arranged with an enlarged central section or compartment 22, a first outer compartment 24, and a second outer compartment 26, each outer compartment having a suitable size generally smaller than that of the central compartment 22. The enlarged central section or compartment 22 is defined by a pair of vertical partitions 28 and 30 (FIGS. 2, 6) which are positioned transversely across the housing so as to establish a flow-through dividing means between the respective outer compartments 24 and 26, thus permitting various solutions to circulate through and across the central section or compartment 22 of reservoir 18 during various steps in the process. Partitions 28 and 30 are mounted so as to abut against a raised perforated platform 32 that defines part of intermediate partition 16 and the base for central compartment 22. A multiplicity of holes or apertures 31 are provided in the platform 32 as a means by which air and/or fluid can pass therethrough during some of the various steps of the process of the present invention. See FIG. 3. A platinum wire grid defines a positive electrode 33 and is positioned against the underside of platform 32 so as to be disposed under the apertures 31, as illustrated in FIG. 3. A positive electrode grid 33 defines the positive side of a vertical transfer operation which will be discussed later.

Accordingly, the central compartment 22 is adapted to receive and support various electrophoresis and transfer components, generally indicated at 35, some of which are illustrated in FIG. 3. A suitable porous support member 34 is positioned over perforated platform 32 of intermediate partition 16. On top of the support member 34 there is positioned a suitable transfer membrane 36, which is defined by a specially treated porous nylon sheet or a material having a comparable attachment capability. Superposed over transfer membrane 36 is a chemically inert material which defines a separation sheet 38 that covers the transfer membrane throughout its length. The separation sheet 38 (which may be made of a suitable plastic) is impervious to liquids and is adapted to be automatically removed by a pulling means, generally indicated at 40 as is illustrated in FIG. 2. The pulling means may be in the form of an electric motor (under the control of the controller to be described) with suitable rollers engaging the sheet and an idler roll 41.

However, it should be noted here that the impervious sheet 38 operates in conjunction with an ultrafine overpressure control means which together define a means to dynamically prevent liquid disposed in reservoir 18 from passing downwardly into the DNA support membrane 36 or further entering the lower chamber 20.

After the separation sheet is in place, a gel member 42 is positioned over it. In gel member 42, as shown in FIG. 3, there is formed a group of typically aligned storage pockets 44 that are arranged to receive various individual DNA samples for the electrophoresis operation. To control the position of the gel member 42 within central compartment 22 a movable automatic positioning means 45 is provided. This positioning means is automatically moved to be located upwardly, as illustrated in FIG. 4, or downwardly, as shown in FIGS. 1 and 2. Positioning means 45 defines a gel weight that comprises a rectangular structure having a substantially flat rectangular frame 47 which is preferably made from a suitable plastic material. A plurality of longitudinal ribs 48 are formed on the underside of the frame so as to contact gel member 42 along thin lines that are parallel to the horizontal electrical field lines generated by means of a conventional negative electrode 23 positioned in compartment 24 of reservoir 18, and a positive electrode 25 positioned in the oppositely disposed compartment 26. Ribs 48 further allow for the evaporation of the electrophoresis buffer solution for cooling purposes. An electric grid consisting of a serpentine stainless steel or platinum wire 44 is mounted to the upper surface of frame 47 and defines a negative electrode 51 for the purpose of establishing a vertical transfer force as referred to above. The grid 44 preferably follows the same pattern as the lower grid or wire 33.

A carriage member 49 is also mounted to frame 47 and comprises a pair of oppositely disposed posts 50 that support a longitudinal beam member 52. (See FIG. 5). In FIGS. 2 and 4, there is shown a support bar 54 to which is mounted a housing 55, a cooling fan 56 and a solenoid 58 being mounted therein. Fan 56 also provides part of the cooling means for the electrophoresis solution Solenoid 58 moves gel weight 45 between and up or down position. Frame 47 is provided with a plurality of aligned holes 60 that allow the buffer solutions stored in reservoir 18 and cooling air to readily pass through frame 47, and also allow the frame to be readily lowered or raised within compartment 22.

Referring again to FIG. 1 and to the basic operation of the apparatus, there is provided a control means which is defined by a central controller or processor 60 which sequentially operates the various components of the apparatus to perform the steps of my process in an automatic continuous manner during the electrophoresis and transfer of DNA or other macromolecules.

To start the process a suitable agarose gel 42, which includes, for example, DNA samples, is loaded and positioned within the central compartment 22 of reservoir 18 along with a suitable and conventional electrophoresis buffer solution e.g., a Tris borate buffer. At the time the electrophoresis buffer is placed in the reservoir, the overpressure generating pump is already turned on manually while later the controller will take over its operation.

It should be noted that the gel can be poured directly into the central compartment (enabling the use of very thin and fragile gels) and the DNA samples can them be placed in the gel pockets 44.

If the gel is actually poured into the central compartment, an additional thin plastic sheet with rectangular bent up side and front walls of about 10 mm high that fits onto and into the central compartment is preferably used on which the combs will rest. After the gel is hardened, the front wall of this thin walled tray (the plastic sheet e.g. made from an overhead transparency sheet, that remains flat under moderate heat) is bent back into the horizontal plane and slipped out from under the gel.

Conventional depurination, denaturation and transfer solutions are also loaded into vessels to be described At this time, the apparatus is turned on, initiating the electrophoresis cycle, wherein the gel and the DNA samples are subjected to a horizontal electric field which causes the DNA charged particles or macromolecules to travel longitudinally through the gel between electrodes 21 and 23 whereby the macromolecules are distributed by their molecular weight along the length of the gel. The application of a suitable d.c. voltage across electrodes 23 and 25, e.g., 50–200 volts, will provide the appropriate field strength for the electrophoresis step.

During the electrophoresis step, which may take between about one-half to two hours, heating occurs. Therefore, cooling fan 56 is provided and operated during this cycle. In addition, the gel weight device 45 is positioned by solenoid 58 to engage and direct the gel downwardly in the position as seen in FIGS. 1 and 2. Accordingly, the gel is gently pressed against the lower inert separation sheet 38. Also, during this operation, chamber 20 is provided with a regulated amount of over-ambient pressure that provides a liquid sealing means between reservoir 19 and air chamber 20 as will be described in more detail.

When the electrophoresis operation is completed, the system is then purged or drained of the electrophoresis solution which flows into a waste container 98 by means of a vacuum pump 100 operated by controller 60. The vacuum pump 100 is connected to the waste container 98 by a vacuum tube 102 and a sealed cap 98a of container 98. A plurality of tubes 104 are arranged to communicate between reservoir 18 at each respective outer compartment 24 and 26, and waste bottle 98. Following the three minute drain cycle the drain pressure is relaxed for approximately ten seconds. The need for this relaxation step lies in the important aspect that the caustic chemicals used in the processing cannot be processed reliably with solenoid valves, but are rather pulled out from the reservoir through several continuous plastic tubings that have a raised section that prevents the liquids from flowing out until they are syphoned and pulled by means of an underpressure generated in he drain bottle 98. After the draining step, however, this underpressure must be completely returned to Zero to prevent the next chemical from syphoning into the drain bottle.

During the electrophoresis step and subsequent steps (prior to transfer), a precisely regulated amount of over-ambient pressure, indicated by arrows 79 in FIG. 4, is created in air chamber 20 located under gel 42. This overpressure establishes an upwardly impinging pressure against the removable impervious sheet 38. This over-ambient air pressure prevents any solution in compartment 22 from leaking or dripping through to contaminate the transfer membrane 36 or entering chamber 20. Thus, a suitable air-pressure means is provided which is illustrated as an air pressure pump 80 having a first conduit or tube 82 with one end thereof connected between the pump outlet and the other end being disposed within the outer compartment 24 at about the level of the separation sheet 38 as shown. A second conduit is connected between the outlet of the pump 80 and the interior of the lower chamber 20 through a solenoid valve means 84. The over-ambient pressure must be precisely maintained so as to be substantially equal to or slightly above (e.g., 1 to 2 mm $H_2O$) the hydrostatic pressure generated by the level of the particular liquid in reservoir 18 in which the gel is sequentially exposed. This pressure is finely regulated by operating an inverted hydrostatic regulator from the chamber 20 defined by a pressure regulating tube 82. The tube 82 serves as a relief valve and is operated directly by the various hydrostatically effective levels and densities of the treating chemicals. This is referred to as "Ultrafine Overpressure Control" and works with a precision of 1 mm of $H_2O$ in the effective range of up to approximately 100 mm of water.

As indicated above, the over ambient-pressure would not by itself prevent the transfer membrane 36 from being exposed to wetting from the overlaid gel, and the membrane would thereby be sequentially exposed to the chemicals within the main reservoir compartment 22 since the gel has to be treated from its underside as well as its topside as is illustrated in FIG. 4. While the above principle prevents substantial penetration of the porous support by any liquid, there is still a need for an additional sealing means to protect the membrane from chemicals on the underside of the gel. Such, a positive sealing means is accomplished by combining the over-ambient air pressure feature and the removable chemically inert separation sheet 38 that is interposed between gel 42 and transfer membrane 36.

The other solutions to be used in the steps following electrophoresis are stored within four containers or bottles 62, 64 66 and 68 and are arranged to communicate with reservoir 18 by means of respective conduits or tubes 70, 72, 74 and 76. A depurination solution 61 of HCl is stored in container 62. A cap 62a seals the top of bottle 62 and is adapted to receive a second tube 70a which defines an air pressure tube, whereby the opposite end of tube 70a is attached to an air pump 78 which supplies air pressure to the interior of container 62. Air pump 78 is activated sequentially by controller 60 which pumps air into container 78 by way of tube 70a, forcing the HCl solution from the container by way of tube 70 into outer compartment 24 of reservoir 18, thereby filling all three reservoir compartments 22, 24 and 26 in about two minutes.

At this time gel weight 45 has been sequentially moved to an upper position by solenoid 50 which is operated by controller 60, as shown in FIG. 4. This allows the gel 42 to float upwardly against the bottom of the gel weight 45.

Accordingly, the depurination solution, surrounds the entire body of gel 42 and is stirred during a fifteen minute incubation period by a stirring means, designated generally at 92. Stir means 92 comprises a drive motor 94 having a suitable paddle wheel 96 located in outer compartment 24. The system is then purged or drained of the depurination 61 via the vacuum pump 100 operated by the controller 60 as was described in connection with the drain step for the electrophoresis solution.

The drain step is followed by the next sequential step in which a quantity of a alkaline denaturation solution 106, containing, for example, NaOH stored in container 64, is pumped into reservoir 18 by means of an air pump 108 that is connected to container 64 by air input tube 70b. Solution 106 flows through tube 72 into outer reservoir compartment 24 filling the three reservoir compartments 22, 24 and 26. This step takes approximately five minutes to complete and is followed by a second incubation period of approximately fifteen minutes at which time stirring means 92 is again activated by controller means 60. This step is followed by another drain cycle, wherein the caustic solution 106 (NaOH) is removed from the system. This takes approximately three minutes followed by a ten second relax drain mode.

A neutralizing Tris buffer solution 109 is pumped from container 66 by air pump 110 through input tube 70c, thereby transferring the Tris buffer from container 66 into reservoir 18 by way of tube 74. This step takes approximately two minutes and is followed by a fifteen minute incubation and stirring cycle which neutralizes the gel. Immediately thereafter the inert plastic sheet 38 is rapidly removed by pulling means 40 which takes approximately three minutes. The Tris buffer solution is drained for three minutes followed by a relaxed drain pressure cycle of ten seconds.

A last solution of low concentration of sodium phosphate 111 having a PH of about 6.5 (transfer buffer) is pumped into the reservoir 18 by means of air pump 112 through air input tube 70d whereby phosphate solution 111 flows through tube 76 into reservoir 18 in approximately five minutes which is then followed by a five minute incubation period during which the transfer buffer is stirred by stirring means 92. Since the impervious sheet 38 has been removed the phosphate solution 111 drips through transfer membrane 36 into porous support member 34. Next the floating gel is forced downwardly by the gel weight 45 until the gel engages the transfer membrane 36. The downward positioning of gel weight 45 takes about thirty seconds. This cycle is followed by the transferring of the denatured DNA fragments by means of a conventional hydrodynamic force (i.e., the vacuum in chamber 20) in combination with a vertical electric field generated between the upper negative horizontal electrode grid 44 and the lower positive electrode grid 33. The controller 60 applies an appropriate d.c. voltage (e.g., within the range of about 4-20 and preferably about 4012 volts d.c.) between the electrodes 44 and 33 to accomplish the vertical electrophoresis operation which takes place together with the conventional vacuum assisted transfer operation. At this time, the cooling fan provides a cooling means to evaporatively remove a substantial portion of the heat generated by the electrotransfer.

The vacuum transfer is provided by a vacuum pump 114 connected to the interior of air chamber 20 by means of vacuum line 116, as is best illustrated in FIG. 2. A pressure regulator 115 limits the low pressure within the lower chamber 20 to about 100 ml Hg. The transfer fluid is continuously pumped back (recirculated) into the upper reservoir by volumetric pump 120 maintaining the transfer fluid level in the reservoir throughout the transfer pump 120 may be a displacement pump (handling about 1 ml/sec., for example) with dual valves and a minimum backflow resistance of, for example, 10-15 cm $H_2O$ in the working direction (i.e, towards the upper reservoir). Without such backflow resistance, the overpressure developed within the lower chamber would escape through the pump. This is the final operation of the process provided by the present invention and takes between about thirty minutes to twelve hours depending upon the specific macromolecules to be transferred and other factors, in particular the concentration and thickness of the gel and molecular weight range of bands to be transferred.

There has thus been described a novel apparatus and method for conducting the electrophoresis and transfer of macromolecules such as nucleic acid (DNA/RNA) fragments and proteins. Various modifications both as to the apparatus and method will become apparent to those skilled in the art without involving any departure from the spirit and scope of my invention as set forth in the appended claims.

I claim:

1. An improved apparatus for automatically conducting electrophoresis of macromolecules positioned within a gel member for sequential separation and transfer of the macromolecules to a transfer membrane, comprising:

a housing having an intermediate horizontal partition defining an upper reservoir and a lower chamber, and wherein a portion of said horizontal partition includes a multiplicity of apertures;

gel positioning means movably mounted within said upper reservoir to position the gel member therein during the sequential operation of electrophoresis and transfer;

means positioned within the reservoir for generating a horizontal-electrical field, whereby the macromolecules are separated horizontally along the length of the gel member;

a plurality of containers in which chemical solutions are stored and sequentially pumped into the reservoir;

pump means operably connected to the containers to pump selected chemical solutions into the reservoir;

a transfer membrane superposed over the apertures of the partition;

a sealing means interposed between said transfer membrane and said gel member, whereby the chemical solutions disposed in the reservoir are prevented from leaking into the transfer membrane and the lower chamber before the transfer of the macromolecules takes place;

means for pressurizing the lower chamber so as to cooperate with the sealing means;

means for removing the sealing means to allow for macromolecules to be vertically transferred to the transfer membrane;

vacuum means in operable communication the lower chamber to provide a sub-with ambient pressure therein whereby the macromolecules are vertically transferred downwardly to the transfer membrane after the sealing means has been removed therebetween;

waste removal means communicating with the reservoir to sequentially remove chemical solutions from the reservoir; and control means operably connected to the pump means, the horizontal electrical field means, the lower chamber pressurizing means, the removing means for the sealing means, the vacuum means and the gel positioning means.

2. An improved apparatus as recited in claim 1 wherein the pressurizing means comprises an inverted hydrostatic regulator arranged to communicate between the lower chamber and the reservoir, whereby an over-ambient pressure is maintained so as to be at least equal to hydrostatic pressure on the sealing means generated by the level of the chemical solution disposed in the reservoir.

3. An improved apparatus as recited in claim 2 wherein the inverted hydrostatic regulator comprises an air pump having an outlet, a first conduit connected between the lower chamber and the outlet of the pump and a second conduit connected at one end to the outlet of the pump and the other end disposed within the reservoir below the anticipated level of the chemical solutions therein whereby the pressure within the lower chamber will remain equal to or above the hydrostatic pressure of the chemical solution on the sealing means.

4. An improved apparatus as recited in claim 3 wherein the inverted hydrostatic pressure regulator's arranged to maintain the pressure within the lower chamber within the range of 0 to 2 mm $H_2O$ with respect to the hydrostatic pressure of the liquid with said chamber on the sealing means.

5. An improved apparatus as recited in claim 4, wherein the reservoir comprises an enlarged central compartment, a first outer compartment, and a second outer compartment, the compartments being defined by a pair of vertical partitions which are positioned transversely across the housing, whereby the chemical solutions disposed in the reservoir flow between the first and second outer compartments, and further including:

stirring means mounted in the reservoir, whereby the chemical solutions are continuously circulated through the reservoir.

6. An improved apparatus as recited in claim 5, wherein the horizontal-electrical field means comprises a negative electrode positioned in said first outer compartment and a positive electrode positioned in said second outer compartment of the reservoir.

7. An improved apparatus as recited in claim 6, wherein the gel positioning means defines a gel weight comprising:

a substantially flat rectangular frame member having a plurality of longitudinal rib members formed on the underside of the frame member so as to contact the gel member along lines that are parallel to the horizontal electrical field lines generated by said oppositely disposed negative and positive electrodes positioned in said reservoir; and means attached to the gel weight for vertically moving said gel weight upwardly and downwardly within the enlarged central compartment of said reservoir.

8. An improved apparatus as recited in claim 1, further including means positioned within the housing for generating a vertically oriented electrical field across the gel member and transfer membrane for assisting in the downward transfer of the macromolecules to the transfer membrane.

9. An improved apparatus as recited in claim 8 further including cooling means for transferring heat away from the membrane during the application of the vertical field.

10. An improved apparatus as recited in claim 9 wherein the cooling means comprises a fan.

11. An improved apparatus as recited in claim 9 wherein the vertical-electrical field means comprises a negative electrode defined by a first wire grid mounted to the gel positioning means and a positive electrode defined by a second wire grid mounted under the multiplicity of apertures of the horizontal partition of the reservoir.

12. An improved apparatus as recited in claim 1 further including a porous support member interposed between the transfer membrane and the partition.

13. A method of automatically conducting electrophoresis of macromolecules positioned within a gel member for sequential separation and transfer of the macromolecules to a transfer membrane, comprising the steps of:

providing a housing having an upper reservoir and a lower chamber formed therein defined by a horizontal partition having a multiplicity of apertures formed in said horizontal partition;

positioning a transfer membrane over the apertures;

positioning a sealing means over the transfer membrane;

positioning a gel member within said reservoir and over the sealing means, a plurality of macromolecule samples being disposed within the gel member;

generating an over-ambient air pressure in the lower chamber for cooperating with the sealing means between the reservoir and the lower chamber to substantially prevent chemical solutions within the upper reservoir from entering the transfer membrane and the lower chamber;

filling the reservoir with an electrophoresis chemical solution so as to envelope the gel member for a selective amount of time;

subjecting the gel member to a horizontal electric field for causing the charged macromolecules to migrate horizontally and longitudinally through the gel member, whereby the macromolecules are distributed by their molecular weight along the length of the gel member;

purging the electrophoresis solution from the reservoir;

filling the reservoir sequentially with at least two additional chemical solutions so as to cover the gel member;

sequentially treating the gel member with the additional chemical solutions for a selected amount of time;

sequentially purging the additional chemical solutions from the reservoir;

removing the sealing means from between the gel member and the transfer membrane; and providing a low pressure within the chamber to transfer the macromolecules to said transfer membrane.

14. The method as recited in claim 13 wherein the step of generating the over-ambient air pressure within the lower chamber Comprises regulating an inverted hydrostatic pressure between said lower chamber and said reservoir until the sealing means is removed from said reservoir, wherein the inverted hydrostatic pressure is directly controlled by the various hydrostatically effective levels and densities of the treating chemical solutions within said reservoir.

15. The method as recited in claim 14 wherein the over-ambient pressure regulating step comprises establishing a pressure within the lower chamber which is within the range of 0 to 2 mm $H_2O$ with respect to the hydrostatic pressure on the sealing sheet.

16. The method as recited in claim 15 wherein said sealing means comprises a sheet of impermeable material attached to a removal means operated by a control means.

17. The method as recited in claim 16, including the step of positioning the gel member in contact with said transfer membrane when said sealing sheet is removed from between said transfer membrane and the gel member.

18. The method of claim 17 further including the step of subjecting the gel member to a vertically oriented electrical field during the time that the lower chamber is subjected to a low pressure to assist in the transfer of the macromolecules from the gel membrane to the transfer membrane 19. The method as recited in claim 18 wherein the step of subjecting the gel member to the vertical electrical field comprises placing a voltage within the range of about 4-20 volts between a negative electrode mounted to said gel positioning means and a positive electrode mounted under the apertures of said horizontal partition.

20. The method as recited in claim 19 further including cooling the gel member during the application of the vertical electrical field.

21. The method as recited in claim 20 wherein each of the positive and negative electrodes of said vertical electric field are defined by a metal grid.

22. A method of automatically conducting electrophoresis of nucleic acid macromolecules positioned within a gel member for sequential separation and transfer of the macromolecules to a transfer membrane comprising the steps of:

providing a housing having an upper reservoir, a lower chamber formed therein and defined by a horizontal partition having a multiplicity of apertures formed in the horizontal partition;

positioning a porous support member over the apertures of said partition;

superposing a transfer membrane over the porous support member;

positioning a substantially impervious sealing sheet over the transfer membrane;

positioning a gel member within said reservoir and above the sealing sheet wherein a plurality of nucleic acid samples are disposed therein;

generating an over ambient air pressure in the lower chamber for cooperating with said sealing sheet to substantially prevent chemical solutions in the upper reservoir from migrating into the transfer membrane and lower chamber;

filling the reservoir with an electrophoresis chemical solution so as to envelope the gel member for a selective amount of time;

subjecting the gel member to a horizontal-electric field causing the charged nucleic macromolecules to travel longitudinally through the gel member, whereby the macromolecules are distributed in accordance with their molecular weight along the length of the gel member;

purging the electrophoresis solution from the reservoir;

filling said reservoir with a depurination chemical solution so as to cover the gel member;

treating the gel member with the depurination solution for a selected amount of time to break the macromolecules into smaller fragments;

purging the depurination solution from the reservoir;

filling the reservoir with a denaturation solution so as to cover the gel member;

treating the gel member with the denaturation solution for a selected amount of time to separate the strands of the macromolecules;

purging the depuration solution from the reservoir;

filling the reservoir with a neutralizing solution so as to cover the gel member;

treating the gel member with the neutralizing solution for a selected amount of time to neutralize any remaining depurination solution within the upper reservoir and gel membrane;

purging the neutralizing solution from the reservoir;

removing said sealing sheet from between the gel and transfer membrane;

positioning the gel member against the transfer membrane;

filling the reservoir with a transfer buffer chemical solution;

treating the gel member with the transfer buffer solution for a selected amount of time; and providing a vacuum within the lower chamber to cause the macromolecules to migrate vertically downwardly from the gel membrane to the transfer membrane.

23. The method of claim 22 further including the step of subjecting the gel member to a vertically oriented electrical field during the time that the lower chamber is subjected to a low pressure to assist in the transfer of the macromolecules from the gel membrane to the transfer membrane.

24. The method of claim 23 further including cooling the gel member during the application of the vertical electrical field.

25. The method as recited in claim 24 wherein the step of subjecting the gel member to the vertical electrical field comprises placing a voltage within the range of about 4–12 volts between a negative electrode mounted to said gel positioning means and a positive electrode mounted under the apertures of said horizontal partition.

26. The method as recited in claim 25 wherein the step of generating the over-ambient air pressure within the lower chamber comprises regulating an inverted hydrostatic pressure between said lower chamber and said reservoir until the sealing means is removed from said reservoir, wherein the inverted hydrostatic pressure is directly controlled by the various hydrostatically effective levels and densities of the treating chemical solutions within said reservoir.

27. The method as recited in claim 26 wherein the over-ambient pressure regulating step comprises establishing a pressure within the lower chamber which is within the range of 0 to 2 mm $H_2O$ with respect to the hydrostatic pressure on the sealing sheet.

* * * * *

UNITED STATES PATENT AND TRADEMARK OFFICE
CERTIFICATE OF CORRECTION

PATENT NO. : 5,279,721
DATED : Jan. 18, 1994
INVENTOR(S) : Peter Schmid

It is certified that error appears in the above-identified patent and that said Letters Patent is hereby corrected as shown below:

Column 1, line 58, after "detection" insert --.--

Column 2, line 8, delete "previous" and insert --pervious--.

Column 3, line 37, after "transfer" insert --.--.

Column 7, line 58, after "described" insert --.--.

Column 11, line 31, after "communication" insert --with--.

Column 13, line 10, "horizontalelectric" should read --horizontal-electric--.

Column 13, line 32, "Comprises" should read --comprises--.

Signed and Sealed this

Fifth Day of July, 1994

Attest:

BRUCE LEHMAN

*Attesting Officer*  *Commissioner of Patents and Trademarks*